United States Patent
Roh et al.

(10) Patent No.: US 11,583,361 B1
(45) Date of Patent: Feb. 21, 2023

(54) ROBOTIC SURGICAL INVENTORY MANAGEMENT

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael D'Andrea, Burlington, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 17/408,404

(22) Filed: Aug. 21, 2021

(51) Int. Cl.
| | |
|---|---|
| *A61B 90/00* | (2016.01) |
| *A61B 34/00* | (2016.01) |
| *A61B 50/33* | (2016.01) |
| *G16H 10/60* | (2018.01) |
| *G06N 10/00* | (2022.01) |
| *G06N 20/00* | (2019.01) |
| *A61B 50/37* | (2016.01) |

(52) U.S. Cl.
CPC .............. *A61B 90/08* (2016.02); *A61B 34/25* (2016.02); *A61B 34/70* (2016.02); *A61B 50/33* (2016.02); *G06N 20/00* (2019.01); *G16H 10/60* (2018.01); *A61B 2034/252* (2016.02); *A61B 2034/254* (2016.02); *A61B 2034/256* (2016.02); *A61B 2050/375* (2016.02); *A61B 2090/0804* (2016.02)

(58) Field of Classification Search
CPC combination set(s) only.
See application file for complete search history.

*Primary Examiner* — Scott Luan
(74) *Attorney, Agent, or Firm* — Perkins Coie LLP

(57) ABSTRACT

A supply tray for a surgical procedure is selected based on the surgical procedure and patient data retrieved from an electronic health records database. Multiple steps of the surgical procedure are retrieved from the electronic health records database. A message is sent to a first manipulator to move a supply from the supply tray to a staging area for performing a step. A first indication is received from a first sensor that the supply is needed at a present time. A position where the supply is needed in an operating area proximate to the staging area is determined using a second sensor. A second message is sent to a second manipulator to move the supply from the staging area to the position. A second indication is received from a third sensor that the step is complete. A third message is sent to a third manipulator to remove the supply.

20 Claims, 11 Drawing Sheets

| Generic Supply Tray | | Total Knee Tray | |
|---|---|---|---|
| Quantity | Description | Quantity | Description |
| 1 | Bag, Beside, Paper | 1 | Bag, Beside, Paper |
| 1 | Table Cover, 50" x 90" (127 x 229 cm) | 1 | Table Cover, 50" x 90" (127 x 229 cm) |
| 1 | Basin, Emesis | 1 | Table Cover, 60" x 90" (127 x 229 cm) |
| 1 | Bowl 32 oz (946 ml), Graduated | 1 | Table Cover, 79" x 90" (127 x 229 cm) |
| 1 | Cautery Pencil, Rckr w/PTFE Tip | 1 | 3/4 Sheet Drape, 53" x 77" |
| 1 | Container, Specimen, 4 oz (120 ml), Lid | 1 | Extremity T Drape |
| 1 | Cup, Medicine, Clear, 2 oz (60 ml) | 1 | Bowl 32 oz (946 ml), Graduated |
| 1 | Foam/Magnetic Needle Counter | 2 | Ring Basin |
| 4 | Drape, Utility, w/Tape, 15" x 26" (38 x 66 cm) | 1 | Flange Tip Yankauer |
| 1 | Instrument Pouch | 1 | Cautery Pencil, Rckr w/PTFE Tip |
| 10 | Gauze, 4" x 4" (10 x 10 cm), 16-Ply | 1 | Transfer Tray, Gold |
| 4 | Gown, Prevention, XL | 1 | Scalpel Holder |
| 1 | Pitcher, 1200 ml | 1 | Mayo Stand Cover |
| 1 | Mayo Stand Cover | 1 | Yankauer, Bulb Tip without Vent |
| 10 | Lap Sponge, 18" x 18" (46 x 46 cm) | 1 | Suction Tubing, 1/4" x 144" |
| 1 | Scalpel Holder | 1 | Stockinette, Impervious, 12" x 48" |
| 1 | Skin/Utility Marker | 4 | Gown, Prevention, XL |
| 1 | Ruler for Skin Marker | 1 | Pitcher, 1200 ml |
| 1 | Strip-Medi, 1/2" x 4" (1 x 10 cm) | 1 | Esmark Bandage, 6" x 9' |
| 1 | Syringe, 10 ml | 1 | Skin/Utility Marker |
| 1 | Syringe, 20 ml | 1 | Ruler for Skin Marker |
| 1 | Syringe, 60 ml | 1 | Coflex Bandage, 6" x 5 yd |
| 5 | Towels | 2 | Undercast Padding, 6" x 4 yd |
| 1 | Bulb Syringe | 1 | Syringe, 10 ml, Leur Lock |
| 10 | Labels | 1 | Bulb Syringe |
| | | 10 | Labels |

*FIG. 5*

| Hospital Inventory | | Generic Tray #123 | | Status -- Patient Jane Doe -- OR#2 -- Right Knee Replacement -- 11:00AM 2/21/21 | | | |
|---|---|---|---|---|---|---|---|
| Quantity | Supply Tray Type | Quantity | Item | Available | Staging | Operating | Receiving |
| 25 | Generic | 1 | Bag, Beside, Paper | | | 1 | |
| 4 | Orthopedic -- Hand | 1 | Table Cover, 50" x 90" (127 x 229 cm) | | | 1 | |
| 6 | Orthopedic -- Shoulder | 1 | Basin, Emesis | | | 1 | |
| 10 | Orthopedic -- Total Knee | 1 | Bowl 32 oz (946 ml), Graduated | | | 1 | |
| 1 | Orthopedic -- Total Hip | 1 | Cautery Pencil, Rckr w/PTFE Tip | | | 1 | |
| ... | ... | 1 | Container, Specimen, 4 oz (120 ml), Lid | | | 1 | |
| 15 | Vascular Minor | 1 | Cup, Medicine, Clear, 2 oz (60 ml) | | | | |
| 5 | Vascular Major | 1 | Foam/Magnetic Needle Counter | | | 1 | |
| | | 4 | Drape, Utility, w/Tape, 15" x 26" (38 x 66 cm) | | | 1 | 1 |
| | | 1 | Instrument Pouch | | | 1 | |
| | | 10 | Gauze, 4" x 4" (10 x 10 cm), 16-Ply | 7 | 1 | 1 | 1 |
| | | 4 | Gown, Prevention, XL | 1 | | 3 | |
| | | 1 | Pitcher, 1200 ml | | | 1 | |
| | | 1 | Mayo Stand Cover | | | 1 | |
| | | 10 | Lap Sponge, 18" x 18" (46 x 46 cm) | 3 | 2 | 2 | 3 |
| | | 1 | Scalpel Holder | | | 1 | |
| | | 1 | Skin/Utility Marker | | | 1 | |
| | | 1 | Ruler for Skin Marker | | | 1 | |
| | | 1 | Strip-Medi, 1/2" x 4" (1 x 10 cm) | | | | |
| | | 1 | Syringe, 10 ml | 1 | | | |
| | | 1 | Syringe, 20 ml | | | 1 | |
| | | 1 | Syringe, 60 ml | | | 1 | |
| | | 5 | Towels | 4 | | 1 | |
| | | 1 | Bulb Syringe | | | 1 | |
| | | 10 | Labels | 4 | | 6 | |

*FIG. 6*

ROBOTIC SURGICAL INVENTORY MANAGEMENT

TECHNICAL FIELD

The present disclosure is generally related to automated and robotic surgical procedures and specifically to systems and methods for robotic surgical inventory management.

BACKGROUND

More than 200 million surgeries are performed worldwide each year and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and amongst the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 5 is a table illustrating example contents of a supply tray, in accordance with one or more embodiments.

FIG. 6 is a table illustrating example contents of a supply database, in accordance with one or more embodiments.

DETAILED DESCRIPTION

Figure 1:
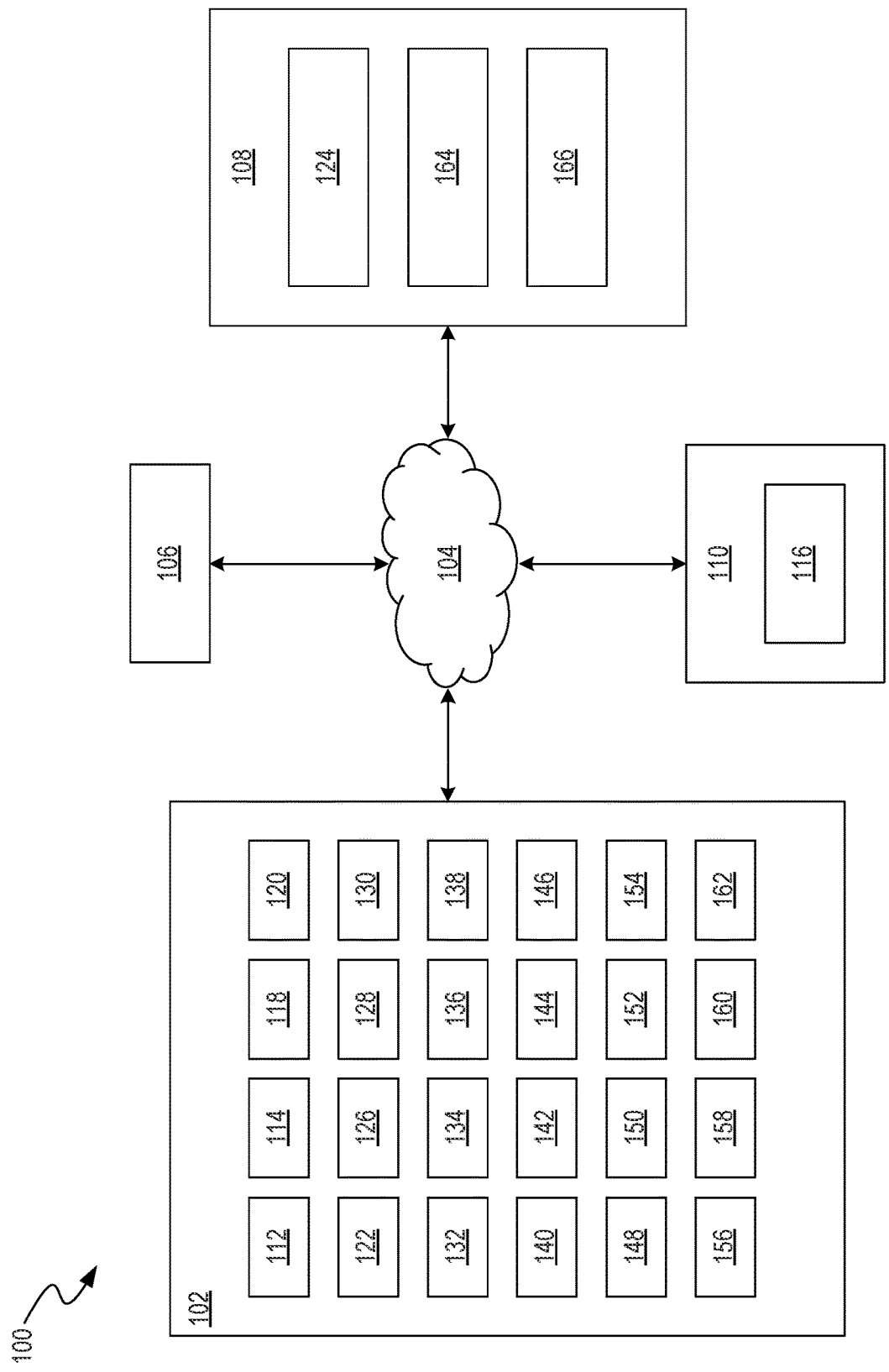
FIG. 1 is a block diagram illustrating an example environment for robotic surgical inventory management, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples.

This document presents methods, systems, and apparatus for robotic surgical inventory management. According to some estimates, as many as 1 in every 1000 surgical procedures result in inadvertently leaving an instrument, needle, or sponge inside a patient during surgery. Such severe surgical errors can lead to complications including infection, and even death. Traditional methods include manually counting instruments and sponges before and after a procedure. According to traditional methods, a manual count of the items involved in a procedure, such as sponges, sharps, tapes, clips, etc., is attempted at least at the beginning and end of the procedure, and a tally kept during the procedure. Tally sheets and whiteboards are used to track counts in conventional systems. In conventional systems, two persons, including the circulating nurse, try to perform both visible and audible counting. Each wound closure point in a procedure is preceded by an examination of the wound area to try not to leave items behind. However, human-based traditional methods suffer from error.

In some embodiments, a system manages surgical supplies for robotic surgery before, during, and/or after a surgical procedure. The surgical supplies needed for a given procedure are identified, monitored by one or more sensors, and maneuvered to an appropriate position for the surgical procedure's current context. The sensors can monitor the present position and/or count of the surgical supplies to identify supply events (e.g., supply faults or discrepancies in the count of surgical supplies) that can indicate a medical error or problem with the surgical procedure. In some embodiments, a surgical plan is evaluated to determine surgical supplies for a robotic surgical system. The surgical supplies can include one or more robotic manipulators, instruments, end effectors, visualization instruments, etc. The system can generate a supply list for items that can be provided in one or more sterilized surgical kits. The surgical kits can include trays holding tools, instruments, etc. In some embodiments, a healthcare provider selects the surgical instruments and other surgical supplies.

At least some embodiments disclosed herein describe selecting a supply tray for a surgical procedure based on the surgical procedure and patient data retrieved from an electronic health records database. Multiple steps of the surgical procedure are retrieved from the electronic health records database. A message is sent to a first manipulator to move a supply from the supply tray to a staging area for performing a step. The message can be a text message, an audible alert, a digital signal, an image displayed on a screen, etc., that the first manipulator can receive and act upon. A first indication is received from a first sensor that the supply is needed at a present time. A position where the supply is needed in an operating area proximate to the staging area is determined using a second sensor. A second message is sent to a second manipulator to move the supply from the staging area to the position. The message can be a text message, an audible alert, a digital signal, an image displayed on a screen, etc., that the second manipulator can receive and act upon. A second indication is received from a third sensor that the step is complete. A third message is sent to a third manipulator to remove the supply. The message can be a text message, an audible alert, a digital signal, an image displayed on a screen, etc., that the third manipulator can receive and act upon. The surgical instruments are grouped into containers (sometimes referred to as trays or kits). In some embodiments, the trays can be moved into position and opened by a circulation nurse who operates outside of the sterile field. The circulation nurse can open a surgical tray allowing a scrub nurse who operates inside the sterile field to remove the sterile instruments or supplies needed for the surgical procedure's current context.

The advantages and benefits of the methods, systems, and apparatus for robotic surgical inventory management disclosed herein include compatibility with best practice guidelines for surgery in an operating room, e.g., from regulatory bodies and professional standards organizations such as the Association for Surgical Technologists. The robotic surgery technologies disclosed offer valuable enhancements to medical or surgical processes through improved precision, stability, and dexterity. The disclosed methods relieve medical personnel from routine tasks and make medical procedures safer and less costly for patients. The embodiments disclosed can also perform more accurate surgery in smaller places and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers advantages, such as no line of sight required, read multiple radio frequency identification (RFID) objects at once, scan at a distance, and flexibility. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning in the disclosed embodiments include the obviation of feature extraction and the use of shared weight in convolutional layers, which means that the same filter (weights bank) is used for each node in the layer; this both reduces memory footprint and improves performance.

FIG. 1 is a block diagram illustrating an example system 100 for robotic surgical inventory management, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The system 100 is implemented using the components of the example computer system 300 illustrated and described in more detail with reference to FIG. 3. Likewise, embodiments of the system 100 can include different and/or additional components, or be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, i.e., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal CO2 monitor or capnography monitor used for measurement of the level of carbon dioxide (referred to as end tidal carbon dioxide, ETCO2) that is released at the end of an exhaled breath. An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. PQRST wave is read as: P wave, which represents the depolarization of the left and right atrium and corresponding to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage, injuries in the organs, aiming at reducing the risk of neurological deficits after operations involving the nervous system. Monitoring is effective in localization of anatomical structures, including peripheral nerves and sensorimotor cortex, which help in guiding the surgeon during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals elicited by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limb, lower limb, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of target site such as pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, cameras are incorporated into a wearable device, such as an augmented reality device like Google Glass, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: A scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theatre tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, and/or xenon halogens and light-emitting diodes (LEDs). Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is are useful and are widely used can be procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of tool—tissue interaction forces. During MIS, the field of view and workspace of tools are compromised due to the indirect access to the anatomy and lack of surgeon's hand-eye coordination. The sensors 134 provide a tactile sensation to the surgeon by providing information of shape, stiffness, and texture of organ or tissue (different characteristics) to the surgeon's hands through a sense of touch. This detection of a tumor through palpation, which exhibits a 'tougher' feel than healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine e.g., positron emission tomography (PET). Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes are used. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems.

The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes are used. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can more widely suit for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body is used. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body is used. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs e.g., vagina) and external imaging (where the transducer is placed on chest for heart monitoring or abdomen for the fetus). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants are used. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location of where they are working in the body. The stereotactic navigation system 138 can be framed (requires attachment of a frame to patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient as well as filter out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform, flex, or extend individual components of the platform, or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theatre or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary position, which is suitable for operation; protect patient from being chilled; and be prepared to meet any emergency.

In some embodiments, the system 100 includes a Jackson frame 144 (or Jackson table), which refers to a frame or table which is designed for use in spine surgeries and can be used in a variety of spinal procedures in supine, prone, or lateral positions in a safe manner. Two peculiar features of the Jackson table 144 are no central table support and an ability to rotate the table through 180 degrees. The Jackson table 144 is supported at both ends which keeps the whole of the table free. This allows the visualization of trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (also referred to as a bair). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The sequential compression device 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; Infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consumes ceiling space and complicates the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter. High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot, and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a tool designed to gradually correct a deformity, e.g., corsets, splints, orthopedic footwear, insoles, and other devices to correct abnormal positions of the foot. A compression-distraction tool refers to a tool designed to correct acquired or congenital deformities of the extremities, e.g., curvature, shortening, and pseudarthrosis such as Gudushauri. A fixation tool can be an internal fixation tool (e.g., screws, plates) or external fixation tool (radius, tibia fracture fixation). The orthopedic tools can be bone-holding forceps, drill bits, nail pins, hammer, staple, etc.

In some embodiments, the tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, rotating bone shearing incision work unit.

In some embodiments, the tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and are used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on material synthetic and natural. Stitches can be based on coating coated and un-coated.

In some embodiments, the tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, tools, or objects is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. A medical equipment can perform diagnosis or provide therapy; for example, the equipment delivers air into the lungs of a patient who is physically unable to breathe, or breaths insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. The ventilator is required when a person is not able to breathe on their own. The ventilator can perform a function of gently pushing air into the lungs (like lungs when they are working) and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse, or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment 102. The consumables 158 can include gloves, gowns, masks, syringes, needles, sutures, staples, tubing, catheters, or adhesives for wound dressing, in addition to other tools needed by doctors and nurses to provide care. Depending on the device, mechanical testing can be carried out in tensile, compression or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, used to tag an instrument with an electronic tag and tracks it using the tag. Typically, this could involve a centralized platform that provides details such as location, owner, contract, and maintenance history for all equipment in real-time. A variety of techniques can be used to track physical assets, including radio-frequency identification (RFID), global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. RFID can be very short for low frequency or high frequency for ultra-high frequency. Managing and locating important assets is a key challenge for tracking medical equipment. Time spent searching for critical equipment can lead to expensive delays or downtime, missed deadlines and customer commitments, and wasted labor. The problem has been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light illuminated and the image seen with the microscope 116 is two dimensional), dissection or stereoscope (light illuminated and image seen with the microscope 116 is three dimensional), confocal (laser-illuminated and image seen with the microscope 116 is on a digital computer screen), scanning electron (SEM) (electron illuminated and image seen with the microscope 116 is in black and white), or transmission electron microscope (TEM) (electron illuminated and image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patients' medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computing device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In some embodiments, the console 108 or the system 10 uses quantum computing. Quantum computing refers to a computational device or method that utilizes properties of quantum states defined by quantum mechanics such as superposition, entanglement, etc., to perform computations. Quantum devices utilize qubits which are the quantum equivalent to bits in a classical computing system. Qubits include at least two quantum states or probable outcomes. These outcomes, combined with a coefficient representing the probability of each outcome, describe the possible states, or bits of data, which can be represented by the qubits according to the principle of quantum superposition. These states can be manipulated which can shift the probability of each outcome or additionally add additional possible outcomes to perform a calculation, the final state of which can be measured to achieve a result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows great promise for drug discovery and simulating the interaction of drugs with biologic systems, however, the same technology can be used to predict the interaction of a biologic system with an implanted device, preventing rejection of an implant by a patient's body, long term function of an implant, and potentially the reaction of a patient to a surgical procedure during a simulation before a procedure or actively during a procedure.

Figure 2:
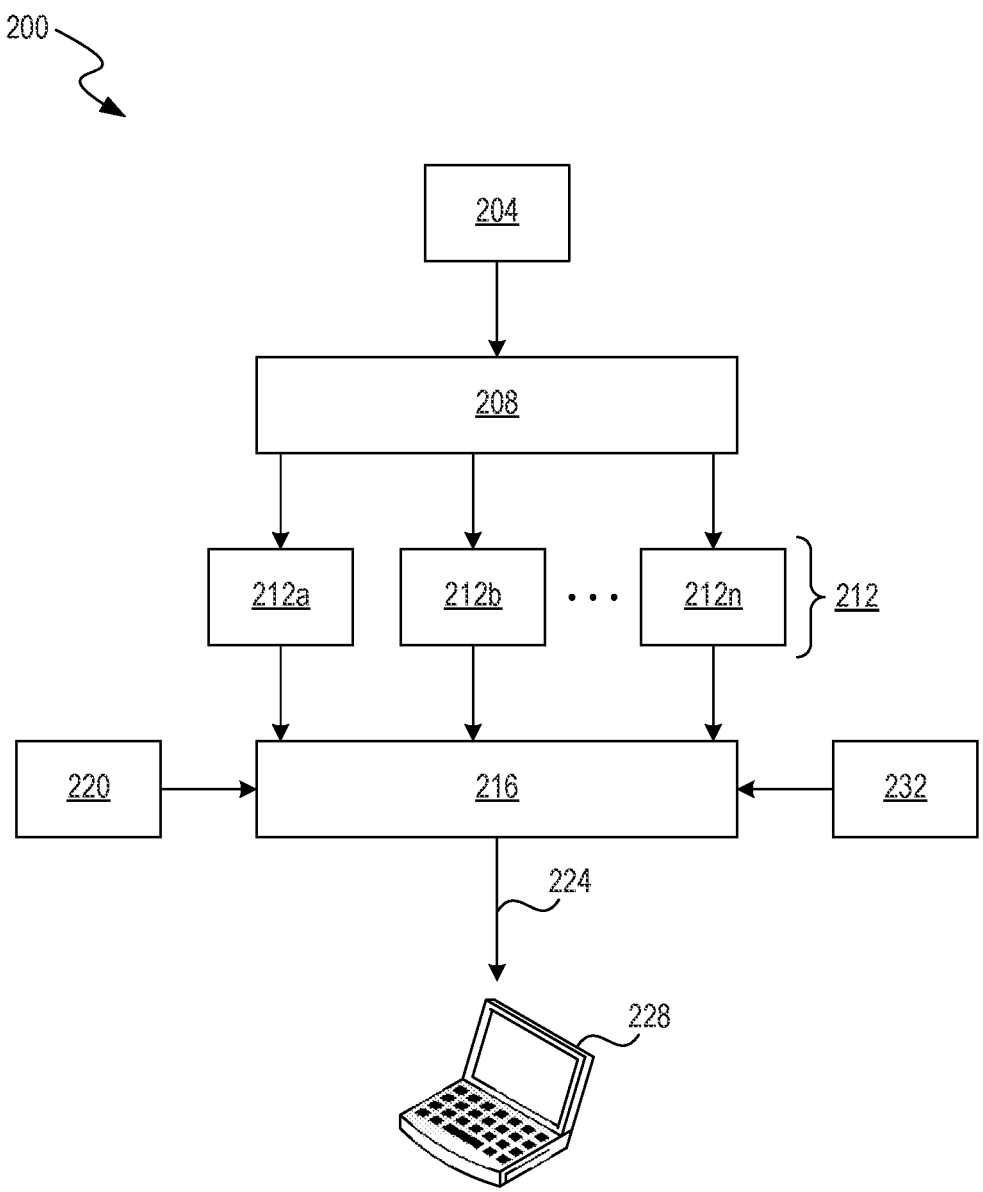
FIG. 2 is a block diagram illustrating an example machine learning system for robotic surgical inventory management, in accordance with one or more embodiments.

FIG. 2 is a block diagram illustrating an example machine learning system 200 for robotic surgical inventory management, in accordance with one or more embodiments. The machine learning system 200 is implemented using components of the example computer system 300 illustrated and described in more detail with reference to FIG. 3. For example, the machine learning system 200 can be implemented on the console 108 using instructions programmed in the memory 164 illustrated and described in more detail with reference to FIG. 1. Likewise, embodiments of the machine learning system 200 can include different and/or additional components, or be connected in different ways. The 200 is sometimes referred to as a machine learning module.

The machine learning system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., features 212a, 212b, and 212n. The feature vector 212 contains the relevant information from the input data 204, such that events or data value thresholds of interest can be identified by the machine learning model 216 by using this reduced representation. In some example embodiments, the following dimensionality reduction techniques are used by the feature extraction module 208: independent component analysis, Isomap, Kernel PCA, latent semantic analysis, partial least squares, principal component analysis, multifactor dimensionality reduction, nonlinear dimensionality reduction, Multilinear Principal Component Analysis, multilinear subspace learning, semidefinite embedding, Autoencoder, and deep feature synthesis.

In alternate embodiments, the machine learning model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the machine learning system 200. For example, the machine learning model 216 can use a cascade of multiple layers of nonlinear processing units for implicit feature extraction and transformation. Each successive layer uses the output from the previous layer as input. The machine learning model 216 can thus learn in supervised (e.g., classification) and/or unsupervised (e.g., pattern analysis) modes. The machine learning model 216 can learn multiple levels of representations that correspond to different levels of abstraction, wherein the different levels form a hierarchy of concepts. In this manner, the machine learning model 216 can be configured to differentiate features of interest from background features.

In alternative example embodiments, the machine learning model 216, e.g., in the form of a convolutional neural network (CNN) generates the output 224, without the need for feature extraction, directly from the input data 204. The output 224 is provided to the computer device 228 or the console 108 illustrated and described in more detail with reference to FIG. 1. The computer device 228 is server, computer, tablet, smartphone, smart speaker, etc., implemented using components of the example computer system 300 illustrated and described in more detail with reference to FIG. 3. In some embodiments, the steps performed by the machine learning system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The machine learning model 216 can be a CNN that includes both convolutional layers and max pooling layers. The architecture of the machine learning model 216 can be "fully convolutional," which means that variable sized sensor data vectors can be fed into it. For all convolutional layers, the machine learning model 216 can specify a kernel size, a stride of the convolution, and an amount of zero padding applied to the input of that layer. For the pooling layers the model 216 can specify the kernel size and stride of the pooling.

In some embodiments, the machine learning system 200 trains the machine learning model 216, based on the training data 220, to correlate the feature vector 212 to expected outputs in the training data 220. As part of the training of the machine learning model 216, the machine learning system 200 forms a training set of features and training labels by identifying a positive training set of features that have been determined to have a desired property in question, and, in some embodiments, forms a negative training set of features that lack the property in question.

The machine learning system 200 applies machine learning techniques to train the machine learning model 216, that when applied to the feature vector 212, outputs indications of whether the feature vector 212 has an associated desired property or properties, such as a probability that the feature vector 212 has a particular Boolean property, or an estimated value of a scalar property. The machine learning system 200 can further apply dimensionality reduction (e.g., via linear discriminant analysis (LDA), principle component analysis (PCA), or the like) to reduce the amount of data in the feature vector 212 to a smaller, more representative set of data.

The machine learning system 200 can use supervised machine learning to train the machine learning model 216, with feature vectors of the positive training set and the negative training set serving as the inputs. In some embodiments, different machine learning techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The machine learning system 200 applies the trained machine learning model 216 to the features of the validation set 232 to quantify the accuracy of the machine learning model 216. Common metrics applied in accuracy measurement include: Precision and Recall, where Precision refers to a number of results the machine learning model 216 correctly predicted out of the total it predicted, and Recall is a number of results the machine learning model 216 correctly predicted out of the total number of features that did have the desired property in question. In some embodiments, the machine learning system 200 iteratively re-trains the machine learning model 216 until the occurrence of a stopping condition, such as the accuracy measurement indication that the machine learning model 216 is sufficiently accurate, or a number of training rounds having taken place.

Figure 3:
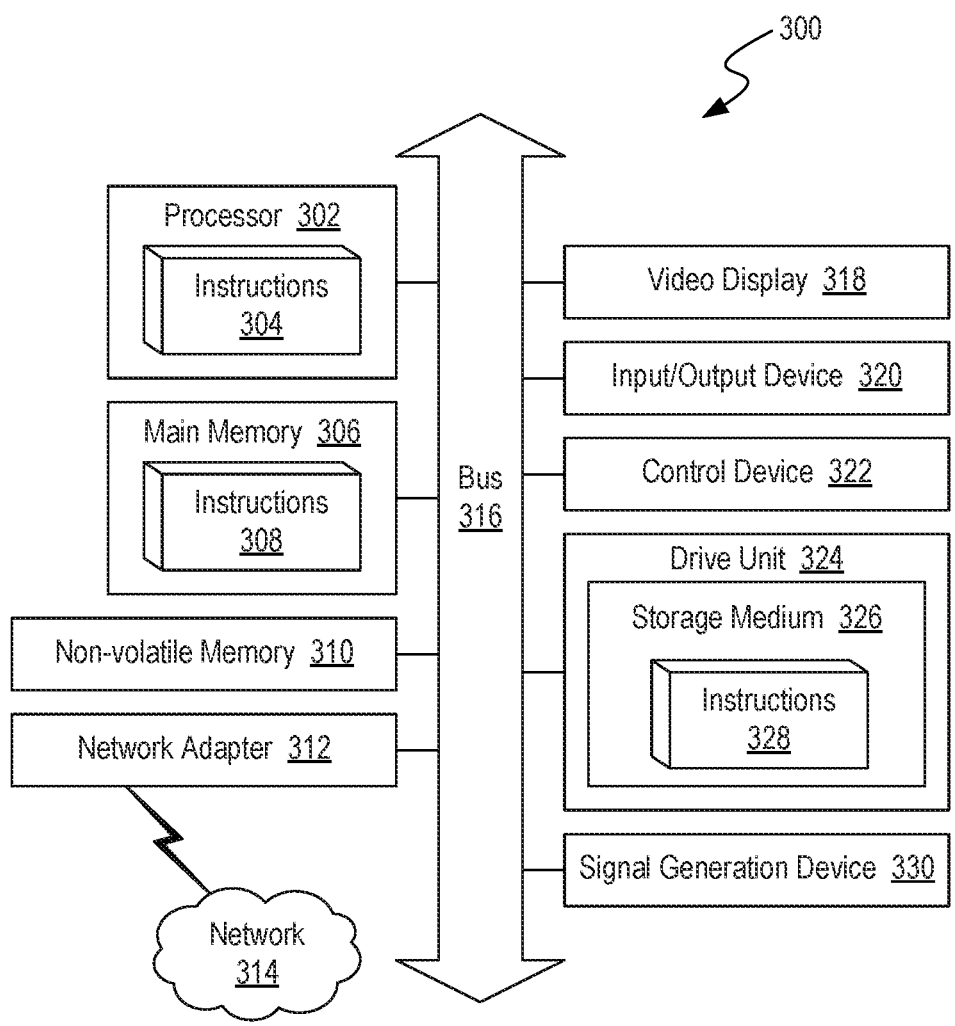
FIG. 3 is a block diagram illustrating an example computer system for robotic surgical inventory management, in accordance with one or more embodiments.

FIG. 3 is a block diagram illustrating an example computer system for robotic surgical inventory management, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the machine learning system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapter 312 (e.g., network interface), video display 318, input/output devices 320, control device 322 (e.g., keyboard and pointing devices), drive unit 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computing device. When read and executed by the one or more processors 302, the instruction(s) cause the computer system 300 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adaptor card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4:
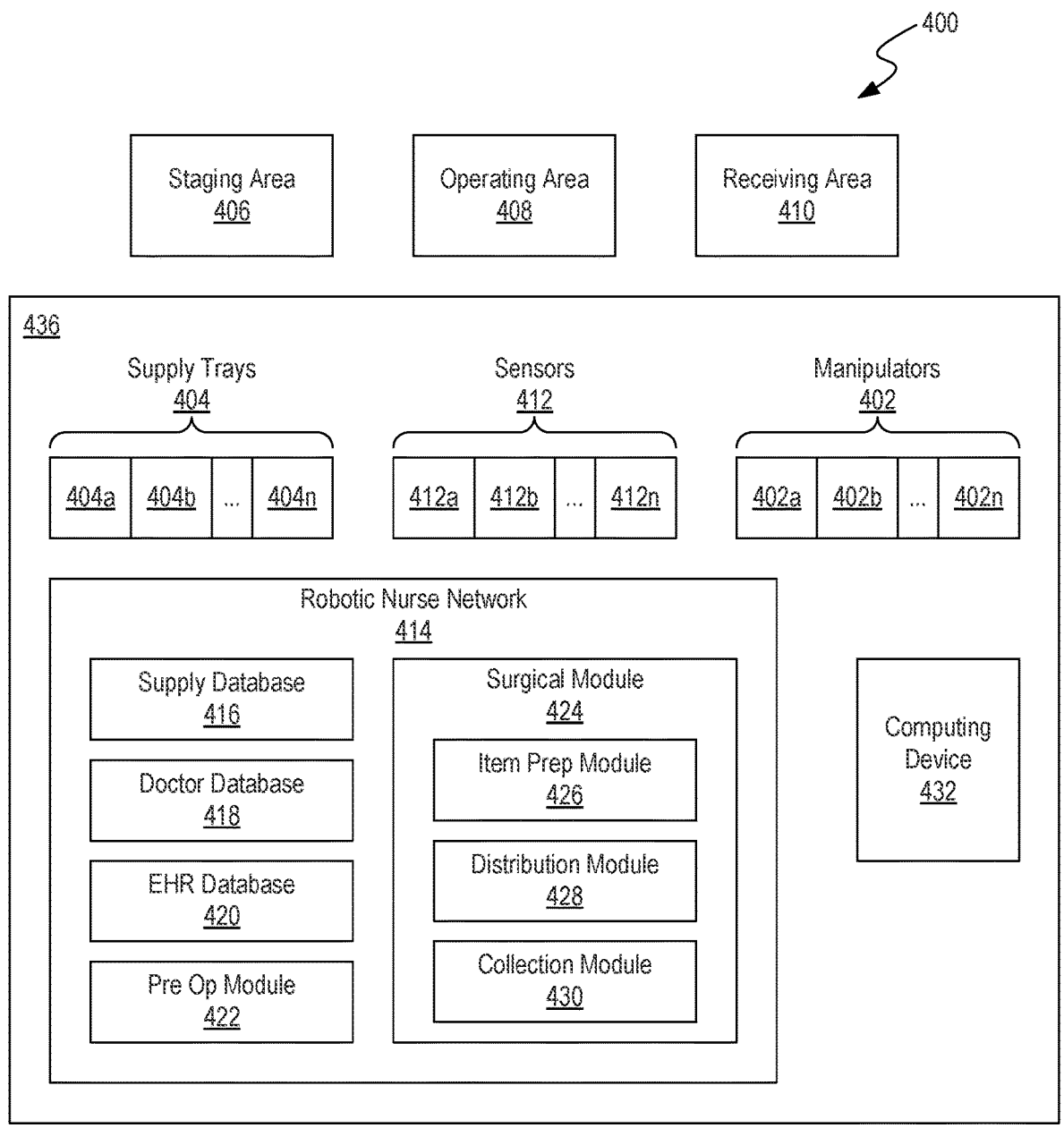
FIG. 4 is a block diagram illustrating an example system for robotic surgical inventory management, in accordance with one or more embodiments.

FIG. 4 is a block diagram illustrating an example environment 400 for robotic surgical inventory management, in accordance with one or more embodiments. The environment 400 includes a staging area 406, operating area 408, receiving area 410, and a system 436 for robotic surgical inventory management. The environment 400 is the same as or similar to the operating room 102 illustrated and described in more detail with reference to FIG. 1. Likewise, embodiments can include different and/or additional components, or the components can be connected in different orders.

The system 436 for robotic surgical inventory management is a computing device, such as a server, computer, or tablet, etc., implemented using components of the example computer system 300 illustrated and described in more detail with reference to FIG. 3. The system 436 for robotic surgical inventory management includes a number "n" of instrument device manipulators 402 (e.g., manipulators 402a, 402b, through 402n), sometimes referred to as "manipulators." The system 436 is the same as or similar to the robotic surgical system 160 illustrated and described in more detail with reference to FIG. 1. In some embodiments, the system 436 includes one or more robotic arms that have an instrument device manipulator on the distal end of each arm that allows the arm to interact with various surgical instruments. The manipulators 402 can assist a scrub nurse and circulation nurse or perform their functions autonomously. There is a sterile field in the operating room 102 to prevent the introduction of germs into the surgical site. In some embodiments, at least one manipulator (e.g., manipulator 402a) is present in the sterile field to handle supplies or instruments in the sterile field. This configuration allows the manipulator 402a in the sterile field to perform some or all of a scrub nurse's functions autonomously. One or more manipulators (e.g., manipulator 402b) outside the sterile field can perform some or all of the functions of a circulation nurse autonomously.

In some embodiments, the two configurations may be used together. For example, the manipulator(s) 402b that are outside the sterile field can retrieve a supply tray 404a of the supply trays 404a, 404b, . . . , 404n from inventory, open the non-sterile packaging, and enable the manipulator(s) 402a that are in the sterile field to prepare supplies or instruments that were not initially in the supply tray(s) 404 for a given procedure. Supplies for a surgical procedure can include tools, such as scissors, clamps, forceps, scalpels, retractors, staplers, clips, laparoscopic instruments, cannulas, reamers, drills, rongeurs, robotic grippers, implants, etc., as illustrated and described in more detail with reference to FIG. 1. The supplies can also include consumables 158 such as drapes, sponges, gauze, etc., as illustrated and described in more detail with reference to FIG. 1.

In some embodiments, the supplies needed are packaged into one or more supply trays (e.g., tray 404b) specific to the procedure. For example, a total knee replacement procedure can have one supply tray (e.g., tray 404b) that includes all of the supplies and instruments needed for the procedure. Another procedure can call for more than one supply tray 404a, 404b. This can be due to the number of supplies needed for a given procedure being too many to practically package in a single supply tray 404b due to size or weight constraints of shipping, operating theater, storage dimensions, and practitioner safety. In addition, to supply trays specific to a given procedure, there can be supply trays (e.g., tray 404n) that are multi-purpose or generic and provide supplies for various procedures and supplies for when there is an unforeseen need for additional supplies during a procedure.

In some embodiments, the robotic nurse network 414 selects a supply tray for a surgical procedure from the supply database 416. The selecting is based on the surgical procedure and patient data retrieved from the EHR database 420. In some embodiments, the environment 400 includes a staging area 406 that is a space for supplies in the procedure's sterile field. In other embodiments, the staging area 406 is not in the sterile field but can be a location where supply trays (e.g., tray 404a) are introduced to the sterile field. For example, the supply tray 404a can be transported to the staging area 406 by a manipulator 402b. The outside of the supply tray 404a may not be sterile. The supply tray 404a can be opened by a manipulator 402b that is not sterile and another manipulator(s) 402a in the sterile field can remove the sterile supplies inside. In some embodiments, the robotic nurse network 414 sends a first message to the manipulator 402b to move a supply from the supply tray 404a to the staging area 406. The supply is for performing a surgical step of the multiple steps of the surgical procedure.

In some embodiments, the environment 400 includes an operating area 408 inside the sterile field and the space in which the procedure is going to be performed. In some embodiments, the environment 400 includes a receiving area 410 for supplies to be placed after being used in the procedure. Supplies introduced into the sterile field are transported through to the receiving area 410 to comply with sterile processing department protocols, even if a particular item is not eventually used.

In some embodiments, the system 436 includes a number a-n of sensors 412a, 412b, . . . , 412n such as optical sensors, microphones, NFC, RFID, etc., used to track the position of supplies and the surgical procedure's context. The sensors are the same as or similar to the monitors 112 and the sensors 134 illustrated and described in more detail with reference to FIG. 1. In some embodiments, some or all of the sensors 412 are integrated into the manipulator(s) 402. In some embodiments, at least one of the sensors 412 is a microphone that receives verbal commands, such as a name of an instrument needed, for robotic surgery. In some embodiments, a sensor 412 is a bar code reader that uses barcode-tagged supplies as part of a tracking system. In some embodiments, a sensor 412 is an RFID reader that uses RFID-tagged supplies as part of an RFID tracking system 162 as illustrated and described in more detail with reference to FIG. 1. In some embodiments, a sensor 412a is a microphone and an indication received is an instruction spoken by a medical practitioner.

In some embodiments, a robotic nurse network 414 is communicatively coupled to the sensors 412 and the manipulators 402. For example, the robotic nurse network 414 can be communicatively coupled via a wired connection, via a cloud or network connection, or over the network 104 illustrated and described in more detail with reference to FIG. 1. The robotic nurse network 414 is a computer, e.g., a desktop, a server, etc., implemented using components of the example computer system 300 illustrated and described in more detail with reference to FIG. 3.

In some embodiments, the robotic nurse network 414 includes a supply database 416 that stores the present availability, contents, and status of each supply tray(s) 404. The status can include which supply tray(s) are assigned to operating theaters, patients, or procedures. The status can also include which items in each supply tray are in the staging area 406, operating area 408, or receiving area 410. In some embodiments, the robotic nurse network 414 includes a doctor database 418 that stores information related to medical providers. In some embodiments, surgeons' preferences, schedules, or procedure history are stored in the doctor database 418.

In some embodiments, the robotic nurse network 414 includes an EHR database 420 that stores patient records. The EHR database 420 is the same as or similar to the EHR 106 illustrated and described in more detail with reference to FIG. 1. Electronic health records are a digital version of patients' paper charts. The EHR database 420 can contain more information than a traditional patient chart, including but not limited to, patient's medical history, diagnoses, medications, treatment plans, allergies, diagnostic imaging, lab results, etc. In some embodiments, the steps for each procedure disclosed herein are stored in the EHR database 420. In some embodiments, the robotic nurse network 414 retrieves multiple steps of a surgical procedure from the EHR database 420.

In some embodiments, the robotic nurse network 414 includes a pre-operative (pre-op) module 422 that enables a surgical procedure to be scheduled, staffed, and supplied. In some embodiments, the robotic nurse network 414 includes a surgical module 424. In some embodiments, the surgical module 424 includes an item prep module 426. In some embodiments, the surgical module 424 uses the sensors 402 to monitor a surgical procedure to enable the item prep module 426 to maneuver supplies from the supply tray(s) 404 to the staging area 406 in advance of the supplies being needed for robotic surgery.

In some embodiments, the surgical module 424 includes a distribution module 428. In some embodiments, the robotic nurse network 414 receives an indication from a sensor 412a that a particular supply is needed at a present time for a present surgical step. In some embodiments, the robotic nurse network 414 sends a message to a manipulator 402a to move a supply from the staging area 406 to a position in the operating area 408. Based on the sensor data, the distribution module 428 is prompted to deliver needed supplies from the staging area 406 via one or more manipulators 402 to the robotic surgical system 160, a practitioner, or to an appropriate part of the operating area 408 at the appropriate time for robotic surgery. The robotic surgical system 160 is illustrated and described in more detail with reference to FIG. 1. The operating area 408 can be monitored by the sensor(s) 412 to identify when supplies need to be removed from the operating area 408 by one or more manipulators 402 and transferred to the receiving area 410. In some embodiments, the robotic nurse network 414 receives an indication from a sensor 412n that a surgical step is complete. Responsive to receiving the indication, the robotic nurse network 414 sends a message to a manipulator 402n to remove a supply from a position in the operating area 408. The surgical module 424 can then update the supply database 416 to ensure that each supply is properly inventoried to prevent inadvertent retention of supplies in a patient and maintain sterile processing department procedures.

In some embodiments, the item prep module 426 uses the information in the EHR database 420 and the supply database 416 to identify the supply tray(s) 404 needed for a given surgical procedure and a position in the receiving area 410 via one or more manipulators 402 at an appropriate time during the surgical procedure. In some embodiments, the distribution module 428 uses the sensors 402 to monitor the operating area 408, the practitioner(s), and the patient to identify the appropriate time and position to deliver supplies from the receiving area 410 to the operating area 408, the robotic surgical system 160, or the practitioner. The robotic surgical system 160 is illustrated and described in more detail with reference to FIG. 1. In some embodiments, a sensor 412a is a camera and an indication is an image. The robotic nurse network 414 performs image recognition on the image to determine that the image indicates a particular supply. In some embodiments, the robotic nurse network 414 performs image recognition using the machine learning model 216 trained on multiple images to generate a determination that a particular image indicates a particular supply.

In some embodiments, the robotic nurse network 414 matches an image to the multiple surgical steps to predict that a next supply will be needed at a next time for a next step of the multiple surgical steps. In some embodiments, the surgical module 424 includes a collection module 430 that is prompted by the surgical module 424 when an item is removed from the operating area 408. The collection module 430 can update the supply database 416 to maintain an accurate count of supplies and prompt a notification when supplies are unaccounted for, indicating inadvertent retention of a supply inside the patient. In some embodiments, the robotic nurse network 414 determines a supply fault based on a mismatch between a first number of supplies in a supply tray 404 and a second number of supplies in the staging area 406, the operating area 408, and the receiving area 410. The robotic nurse network 414 generates a notification based on the supply fault.

In some embodiments, the system 436 includes a computing device 432 that enables a practitioner or hospital administrator to interact with the robotic nurse network 414 to schedule surgical procedures using the pre-op module 422. The computing device 432 can be a computer, smartphone, tablet, etc., that is directly connected to the robotic nurse network 414 or communicatively coupled via a cloud, wireless connection, or over the network 104. In some embodiments, the computing device 432 is the console 108 illustrated and described in more detail with reference to FIG. 1.

In some embodiments, the robotic nurse network 414 retrieves a supply list specifying items for a surgical supply tray 404 selected for a surgical procedure from a supply database 416. Example contents of the supply tray 404 are illustrated and described in more detail with reference to FIG. 5. The robotic nurse network 414 monitors presence and a location of each item of the surgical supply tray 404. The robotic nurse network 414 determines absence of an item for the surgical supply tray 404 based on the monitoring and the supply list. In response to determining absence of the item, the robotic nurse network 414 sends a notification to a computer device, e.g., the computer device 432. In some embodiments, the notification is sent to a user of the computer device 432 or a robotic surgical system 160. The robotic surgical system 160 is illustrated and described in more detail with reference to FIG. 1. In some embodiments, sending the notification includes providing one or more of an audible alarm, a visual alarm, or haptic feedback.

In some embodiments, the robotic nurse network 414 transmits a request for the item prior to a start of the surgical procedure. In some embodiments, the robotic nurse network 414 modifies a surgical plan based on the item. The robotic nurse network 414 tracks each of the items for the surgical supply tray 404 to be used in the modified surgical plan. In some embodiments, the robotic nurse network 414 determines a supply fault based on a mismatch between a first number of supplies in a supply tray 404 and a second number of supplies in a staging area 406, an operating area 408, and a receiving area 410. The robotic nurse network 414 generates the notification based on the supply fault. In some embodiments, the items are monitored, by the robotic nurse network 414, during the surgical procedure. In some embodiments, the robotic nurse network 414 use an optical sensor (e.g., sensor 412a) to identify items of the surgical supply tray 404. In some embodiments, the optical sensor 412a includes at least one of a bar code reader or a camera.

In some embodiments, the robotic nurse network 414 retrieves a supply list from the supply database 416. The supply list specifies items in each of multiple surgical supply trays 404 selected for a surgical procedure. The robotic nurse network 414 tracks presence and/or location of each item in each of the multiple surgical supply trays 404. The robotic nurse network 414 determines that at least one item is missing from at least one (e.g., tray 404a) of the multiple surgical supply trays 404 based on the supply list. In response to determining that the at least one item is missing, the robotic nurse network 414 performs a missing item recovery action to enable completion of the surgical procedure. In some embodiments, the missing item recovery action includes retrieving, by the robotic nurse network 414, another surgical tray (e.g., tray 404b) of the multiple surgical supply trays 404 having the at least one item.

In some embodiments, determining that the at least one item is missing is performed prior to a scheduled start time of the surgical procedure. In some embodiments, the robotic nurse network 414 displays a schedule for using the items in each of the multiple surgical supply trays 404 in the surgical procedure. In some embodiments, the robotic nurse network 414 determines whether each of the items in each of the multiple surgical supply trays 404 selected for a surgical procedure is present.

FIG. 5 is a table 500 illustrating example contents of a supply tray 404, in accordance with one or more embodiments. The supply tray(s) 404 are illustrated and described in more detail with reference to FIG. 4. To maintain the sterile field in an operating room 102 during a surgical procedure, the operating room 102 is stocked with some number a-n of supply trays 404 that contain supplies and instruments that can be specific to a given surgical procedure. The operating room 102 is illustrated and described in more detail with reference to FIG. 1. For example, a generic supply tray 404a can contain supplies needed in a large number of surgical procedures, such as table covers, gauze, skin markers, scalpel holders, syringes, needle counters, bowls, towels, drapes, or gowns. Likewise, embodiments can include different and/or additional contents, or the components can be organized in different ways.

A supply tray 404b that is specific to a given surgical procedure, such as a total knee replacement, can have some number of items in it that are also in a generic supply tray and items that are specific to a total knee replacement. For example, a total knee replacement supply tray 404b can have some or all of the items in a generic supply tray 404a as well as different quantity and or sizes of drapes, syringes, bowls, table covers, bandages, dressings, etc., as well as additional items such as a stockinette, or undercast padding. Multiple trays can be used for any given surgical procedure.

FIG. 6 is a table 600 illustrating example contents of a supply database 416, in accordance with one or more embodiments. The supply database 416 is illustrated and described in more detail with reference to FIG. 4. The supply database 416 can store a number of each type of supply tray 404 presently in the hospital's inventory. Likewise, embodiments can include different and/or additional contents, or the components can be organized in different ways. In some embodiments, the supply database 416 stores a status of a particular supply tray (e.g., supply tray 404b). The status of the supply tray 404b can include an identity of a patient, a surgical pro4edure, a time, or a location in which the supply tray 404b will be used.

The pre-op 422 module can be used to assign a generic supply tray (e.g., supply tray 404a) an identification number (e.g., ID #123). The pre-op 422 module is illustrated and described in more detail with reference to FIG. 4. For example, the generic supply tray 404a is assigned to Operating Room 2 on February 21 of 2021, for a right knee replacement for patient Jane Doe, for example. Each item's status in the generic supply tray ID #123 can be tracked or updated by the surgical module 424, the item prep module 426, the distribution module 428, or the collection module 430. The surgical module 424, the item prep module 426, the distribution module 428, and the collection module 430 are illustrated and described in more detail with reference to FIG. 4.

Figure 7:
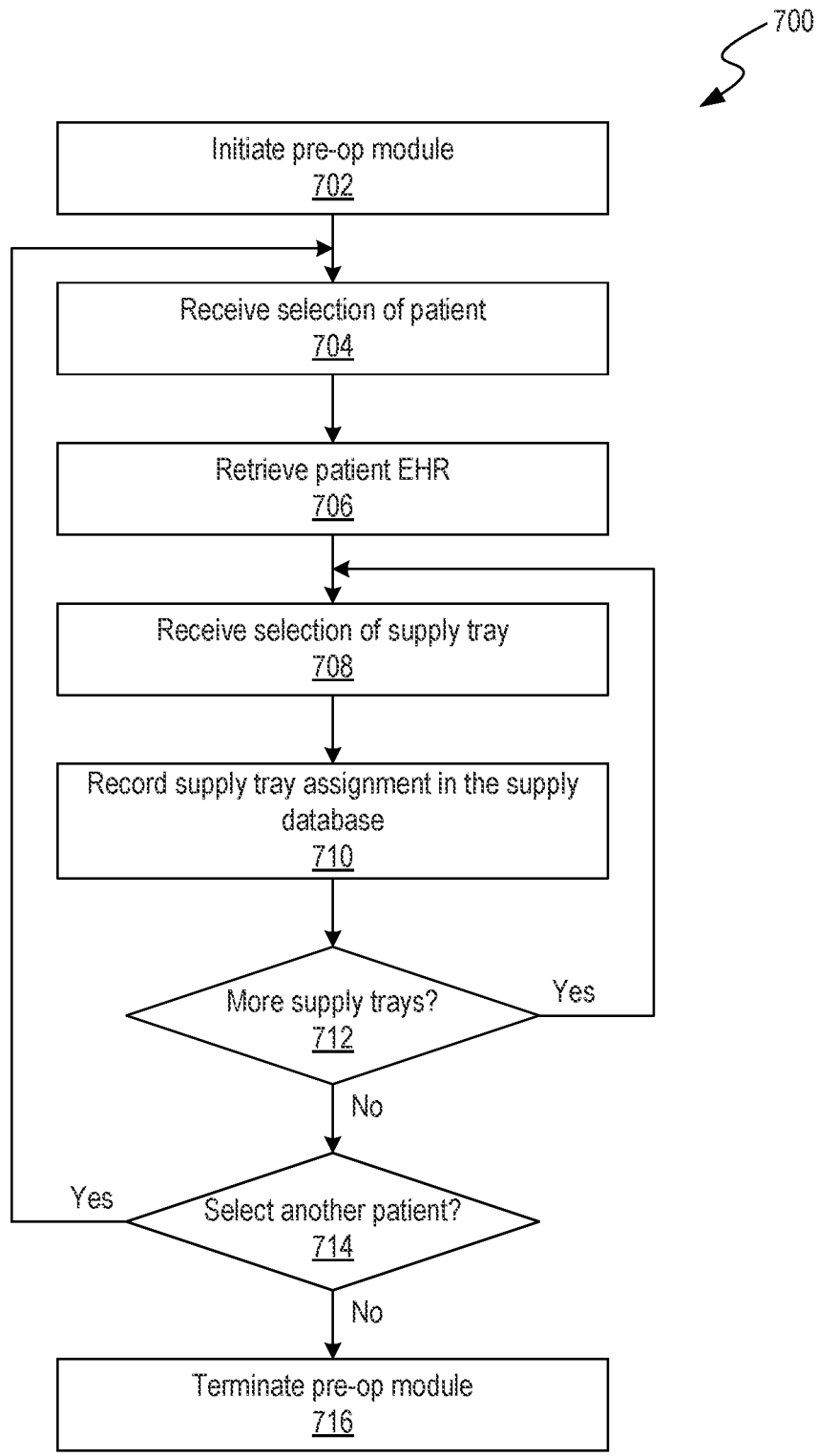
FIG. 7 is a flow diagram illustrating an example process for robotic surgical inventory management, in accordance with one or more embodiments.

FIG. 7 is a flow diagram illustrating an example process 700 for robotic surgical inventory management, in accordance with one or more embodiments. In some embodiments, the example process 700 is performed by the pre-op module 422 illustrated and described in more detail with reference to FIG. 4. In other embodiments, the process 700 of FIG. 7 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 702, the pre-op module 422 is initiated. The pre-op module 422 is initiated when it receives a user's credentials from the computing device 432. The computing device 432 is illustrated and described in more detail with reference to FIG. 4. In step 704, the pre-op module 422 receives a selection of a patient (identification, data, or chart) from the computing device 432. The patient is listed in the EHR database 420. The EHR database 420 is illustrated and described in more detail with reference to FIG. 4. In step 706, the pre-op module 422 retrieves an electronic health record for the indicated patient from the EHR database 420.

In some embodiments, the robotic nurse network 414 selects a supply tray for a surgical procedure from the supply database 416. The selecting is based on the surgical procedure and patient data retrieved from the EHR database 420. For example, in step 708, the pre-op module 422 receives, from the computing device 432, a user selection of a supply tray (e.g., supply tray 404a) from the supply database 416 that is to be assigned to a given patient, procedure, date, time, or location. The supply tray 404a and supply database 416 are illustrated and described in more detail with reference to FIG. 4. In step 710, the pre-op module 422 records the selection of the given supply tray 404a in the supply database 416. For example, patient Jane Doe has a right knee replacement procedure being performed in Operating Room number 2 on Feb. 21, 2021, at 11:00 AM and has generic supply tray ID#123 assigned to that procedure. A single surgical procedure can have multiple supply trays 404a, 404b assigned to it.

In step 712, the pre-op module 422 receives, from the computing device 432, an indication that another supply tray (e.g., 404b) should also be assigned to the present patient or surgical procedure. For example, an indication that another supply tray 404b is to be assigned to Jane Doe's right knee replacement. Supply tray 404b can be, for example, a total knee replacement tray. In such an event, the pre-op module 422 returns to step 708 to receive the selection of additional supply trays 404 from the computing device 432. Say, at step 712, there is no indication, from the computing device 432, of additional supply tray(s) 404 to be assigned to the present surgical procedure. In such an event, at step 714, the pre-op module 422 can receive an indication from the computing device 432 of another patient selection. At step 714, if the computing device 432 indicates that another patient is to be selected, the pre-op module 122 will return to step 704 to perform the necessary selection. If the computing device 432 does not indicate, at step 714, that additional patients are to be selected, the pre-op module 122 terminates the session at step 716.

Figure 8:
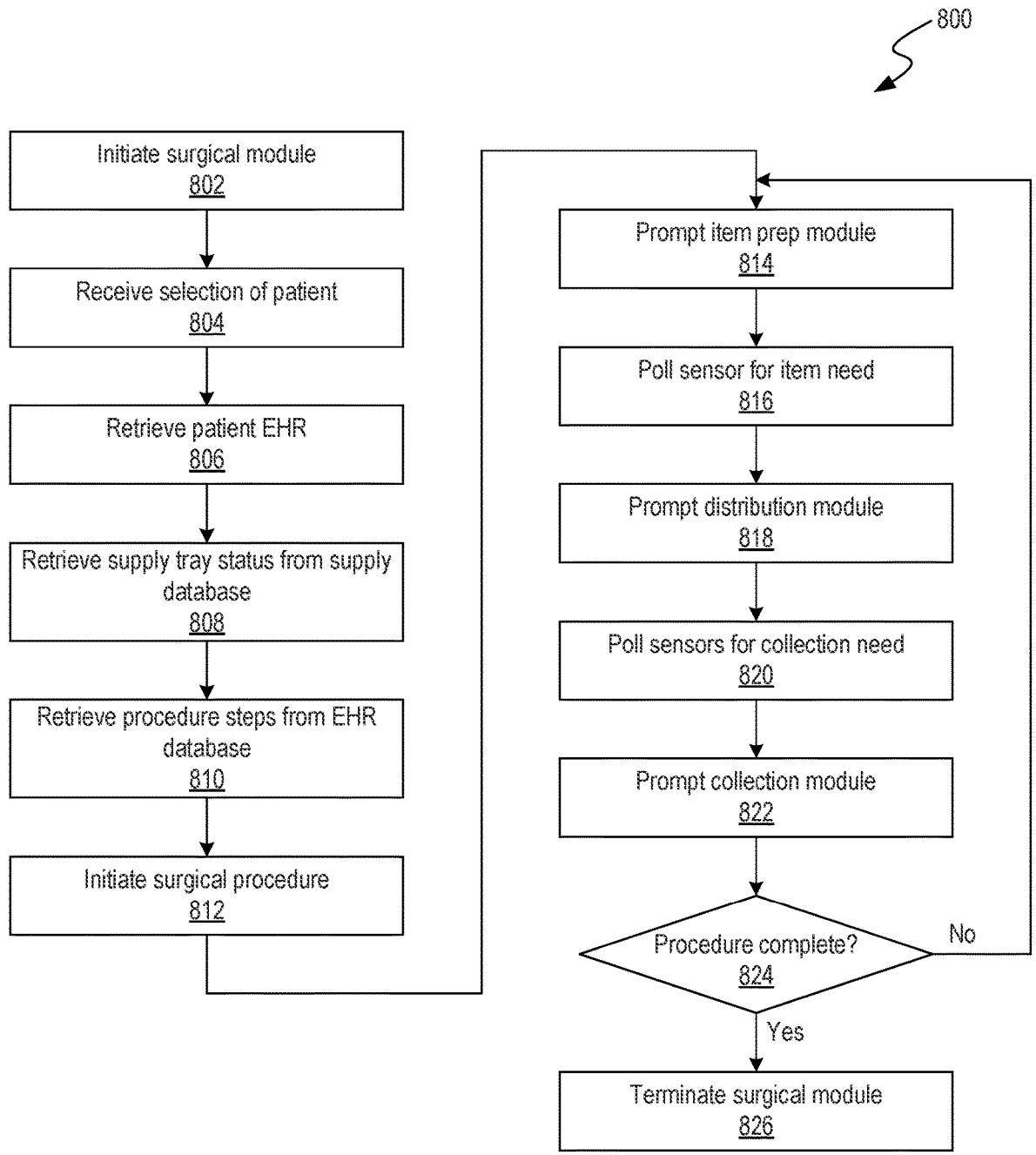
FIG. 8 is a flow diagram illustrating an example process for robotic surgical inventory management, in accordance with one or more embodiments.

FIG. 8 is a flow diagram illustrating an example process 800 for robotic surgical inventory management, in accordance with one or more embodiments. In some embodiments, the example process 800 is performed by the surgical module 424 illustrated and described in more detail with reference to FIG. 4. In other embodiments, the process 800 of FIG. 8 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 802, the surgical module 424 is initiated. For example, the surgical module 424 receives an indication from the computing device 432 that a user, generally a practitioner such as a doctor, nurse, or technician, has logged in. The computing device 432 is illustrated and described in more detail with reference to FIG. 4. In step 804, the surgical module 424 receives a selection of a patient from the computing device 432. For example, an orthopedic surgeon selects patient Jane Doe using the computing device 432. In step 806, the surgical module 424 retrieves the EHR for patient Jane Doe from the EHR database 420. The EHR database 420 is illustrated and described in more detail with reference to FIG. 4. In some embodiments, the robotic nurse network 414 retrieves multiple steps of a surgical procedure from the EHR database 420. In some embodiments, the EHR indicates the surgical procedure Jane Doe is scheduled to undergo, such as a right knee replacement. In some embodiments, the EHR includes the individual steps in a total knee replacement that can include the supplies needed at each step and indicators of each step, potential errors, or emergencies.

In step 808, the surgical module 424 retrieves the status of all supply trays 404 assigned to the present surgical procedure from the supply database 416. The supply trays 404 and the supply database 416 are illustrated and described in more detail with reference to FIG. 4. For example, patient Jane Doe has a total knee replacement supply tray ID #456 and generic supply tray ID #123 assigned to their full right knee replacement procedure schedule for 11:00 AM on Feb. 21, 2021, in Operating Room 2.

In step 810, the surgical module 424 retrieves the detailed steps of the total knee replacement, including necessary indications, from the EHR database 420. In some embodiments, a sensor 412a is a camera and an indication is an image. The robotic nurse network 414 performs image recognition on the image to determine that the image indicates a particular supply. The indications can vary depending upon the embodiment. In some embodiments, the indications are keywords that are picked up by a microphone, such as "sponge" or "suction" or "making an incision." In some embodiments, the robotic nurse network 414 receives an indication from a sensor 412a that a particular supply is needed at a present time for a present surgical step. In some embodiments, the indications are images that an optical recognition system can search for. In some embodiments, the optical recognition system is part of the robotic surgical system 160 illustrated and described in more detail with reference to FIG. 1. For example, an incision site can be monitored for incision size to determine when the incision step is completed. Such an indication can signal the need for a clamp to hold the incision site open. In some embodiments, the indicators include image data received from one or multiple cameras. Such cameras are illustrated and described in more detail with reference to the monitors 112 in FIG. 1.

The image data can in turn be analyzed by an optical recognition system, which is capable of matching the image data to at least a portion of the surgical plan. The matched portion of the surgical plan can be used as indicators to predict at least one other portion of the surgical plan. In some embodiments, the robotic nurse network 414 matches an image to the multiple surgical steps to predict that a next supply will be needed at a next time for a next step of the multiple surgical steps. For example, image data from patient Jane Doe's total knee replacement surgery can indicate that the implant has been successfully implanted in the patient and surgical tools used for the implantation have been removed. Such an indication can further indicate that the implantation step has been completed and that the surgery will now proceed to the next step. The next surgical step may be, for example, suturing the incision site. In such an event, the item prep module 426 is prompted to move the supplies necessary for suturing the incision site to the staging area 406. The item prep module 426 and the staging area 406 are illustrated and described in more detail with reference to the monitors 112 in FIG. 4.

In step 812, the surgical procedure itself is initiated. In some embodiments, the robotic nurse network 414 sends a first message to the manipulator 402b to move a supply from the supply tray 404a to the staging area 406. The supply is for performing a surgical step of the multiple steps of the surgical procedure. For example, in step 814, the surgical module 424 prompts the item prep module 426 to move the supplies necessary for the present surgical step in the surgical procedure to the staging area 406. For example, if the next step in a surgical procedure calls for two sponges and a scalpel, those items can be positioned by one or more manipulators 402 in the staging area 406. The manipulators 402 are illustrated and described in more detail with reference to FIG. 4. In some embodiments, a first manipulator 402b is located outside a sterile field and a second manipulator 402a is located inside the sterile field. In some embodiments, the supply tray(s) 404 are positioned in a cabinet by the robotic surgical system 160 such that one or more manipulators 402 in the sterile field can retrieve the needed item from the supply tray without violating the sterile field. The robotic surgical system 160 is illustrated and described in more detail with reference to the monitors 112 in FIG. 1. In some embodiments, one or more manipulators 404 outside the sterile field autonomously perform some or all of a circulation nurse's functions.

In step 816, once the item prep module 126 has been prompted, the surgical module 424 polls the sensors 412 to indicate an item need. In some embodiments, a sensor 412a is a microphone and an indication received is an instruction spoken by a medical practitioner. The indication can be a surgeon or nurse indicating the surgical step or supply item needed at a given time. The indication can also be a visual indication, such as bleeding. The optical recognition system can recognize the bleeding as an indication of the need for a sponge. The optical recognition system receives imaging data from multiple imagining devices, for example, the imaging system 136 illustrated and described in more detail with reference to FIG. 1. The multiple imaging devices can include, for example, cameras attached to the manipulators 402, cameras mounted to the ceiling or other above the surgical theater, cameras mounted on a tripod or other independent mounting device, cameras that are body worn by a surgeon or other surgical staff, cameras that are incorporated into a wearable device, such as an augmented reality device like Google Glass, cameras that are integrated to an endoscopic, microscopic, laparoscopic, or any camera or other imaging device (e.g. ultrasound) that may be present in the operating room 102. The operating room 102 is illustrated and described in more detail with reference to FIG. 1.

In some embodiments, the robotic nurse network 414 performs image recognition using the machine learning model 216 trained on multiple images to generate a determination that a particular image indicates a particular supply. For example, the optical recognition system can execute an algorithm or software module capable of determining qualitative or quantitative data from medical images, which can be, for example, a deep learning algorithm that has been trained on a data set of medical images. In some embodiments, the machine learning system 200 illustrated and described in more detail with reference to FIG. 2 is used. The medical images serve as the input data 204, the data set of medical images serve as the training data 220, and the deep learning algorithm serves as the machine learning model 216. The input data 204, training data 220, and machine learning model 216 are illustrated and described in more detail with reference to FIG. 2.

In step 818, upon receiving an item need indication, the surgical module 424 prompts the distribution module 428. The distribution module 428 is illustrated and described in more detail with reference to FIG. 4. In step 820, once the distribution module 428 has been prompted, the surgical module 424 prompts the sensors 412, indicating a need to collect an item from the operating area 408. The sensors 412 and the operating area 408 are illustrated and described in more detail with reference to FIG. 4. The indication can be a message from the robotic surgical system 160 illustrated and described in more detail with reference to FIG. 1. The indication can be an audible command from a medical practitioner. The indication can be a visual indication, such as a movement of a medical practitioner's hand with the supply item in it in a specific context. In some embodiments, the robotic nurse network 414 receives an indication from a sensor 412*n* that a surgical step is complete. For example, the practitioner removing a sponge from an incision site can be a visual indication that the sponge needs to be moved from the operating area 408 to the receiving area 410.

Responsive to receiving the indication, the robotic nurse network 414 sends a message to a manipulator 402*n* to remove a supply from a position in the operating area 408. For example, in step 822, upon receiving an indication of a need to remove an item from the operating area 408, the surgical module 424 prompts the collection module 430. The collection module 430 is illustrated and described in more detail with reference to FIG. 4. In step 824, once the collection module 430 has been prompted, the surgical module 424 determines whether the surgical procedure is complete. In some embodiments, the surgical module 424 receives a verbal indication from a practitioner that the surgical procedure is completed. In some embodiments, completing the last step in the surgical procedure as defined in the EHR database 420 indicates the surgical procedure is completed. For example, the last step can be applying a bandage of a particular type. When the optical recognition system detects that bandage type has been applied to a specific area of the patient, the optical recognition system indicates the surgical procedure's completion. If the surgical procedure is not complete, the surgical module 124 returns to step 814. If the surgical procedure is complete, the program ends at step 826.

Figure 9:
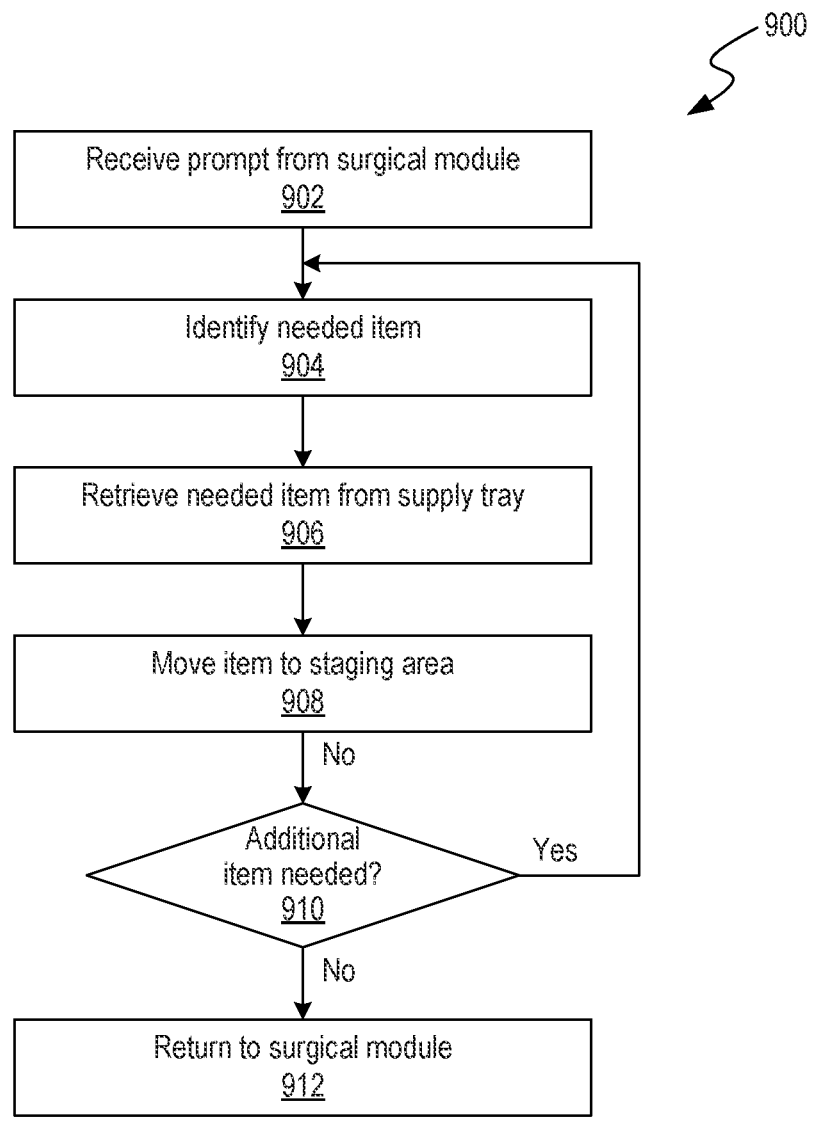
FIG. 9 is a flow diagram illustrating an example process for robotic surgical inventory management, in accordance with one or more embodiments.

FIG. 9 is a flow diagram illustrating an example process 900 for robotic surgical inventory management, in accordance with one or more embodiments. In some embodiments, the example process 900 is performed by the item prep module 426 illustrated and described in more detail with reference to FIG. 4. In other embodiments, the process 900 of FIG. 9 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 902, the item prep module 426 initiates a session when it receives a prompt from the surgical module 424. The surgical module 424 is illustrated and described in more detail with reference to FIG. 4. The prompt includes the surgical procedure's current status and the item or items needed from the supply tray(s) 404. The supply trays 404 are illustrated and described in more detail with reference to FIG. 4. In some embodiments, responsive to receiving an indication from a sensor, the robotic nurse network 414 determines a position where a particular supply is needed in the operating area 408 that is proximate to the staging area 406. The determining is based on data from the sensor 412. For example, in step 904, the item prep module 426 identifies a physical position of the needed supply item. In some embodiments, the robotic surgical system 160 or a circulation nurse opens a supply tray 404 and positions it such that a manipulator 402 in the sterile field can remove needed items without violating the sterile field. The robotic surgical system 160 is illustrated and described in more detail with reference to FIG. 1. The manipulator 402 is illustrated and described in more detail with reference to FIG. 4. An optical sensor can be used with an object recognition system to identify each supply item in the supply tray 404 and each supply item's position/location/orientation. In some embodiments, the object recognition system is part of the robotic surgical system 160 illustrated and described in more detail with reference to FIG. 1.

In step 906, the item prep module 426 prompts retrieval of the needed supply item from the supply tray 404. For example, a manipulator 402 can retrieve the needed supply item with a magnetic attachment, adhesive surface, or grasping mechanism. In some embodiments, the item prep module 426 delivers audibly or displayed instructions to a circulation or scrub nurse indicating which supply item needs to be brought to the staging area 406. The staging area 406 is illustrated and described in more detail with reference to FIG. 4. In some embodiments, there are multiple manipulators 402, each with a supply item, configured on a clothesline type connection that enables the manipulator (e.g., manipulator 402*a*) having the needed supply item to be maneuvered into the proper position. In some embodiments, one or more manipulators 402 have a fixed mounting point and a range of motion that allows them to reach at least two of the supply tray(s) 404, staging area 406, operating area 408, and receiving area 410. The operating area 408 and receiving area 410 are illustrated and described in more detail with reference to FIG. 4.

In step 908, the item prep module 426 moves the retrieved supply item to the appropriate position in the staging area 406. The supply item is maneuvered to the appropriate orientation to allow the supply item to be later transferred from the staging area 406 to the operating area 408. In step 910, the item prep module 426 determines whether an additional supply item is needed in the staging area 406. If another supply item is needed, the item prep module 426 returns to step 904. If no additional supply item is needed, the item prep module 426 returns control, at step 912, to the surgical module 424.

Figure 10:
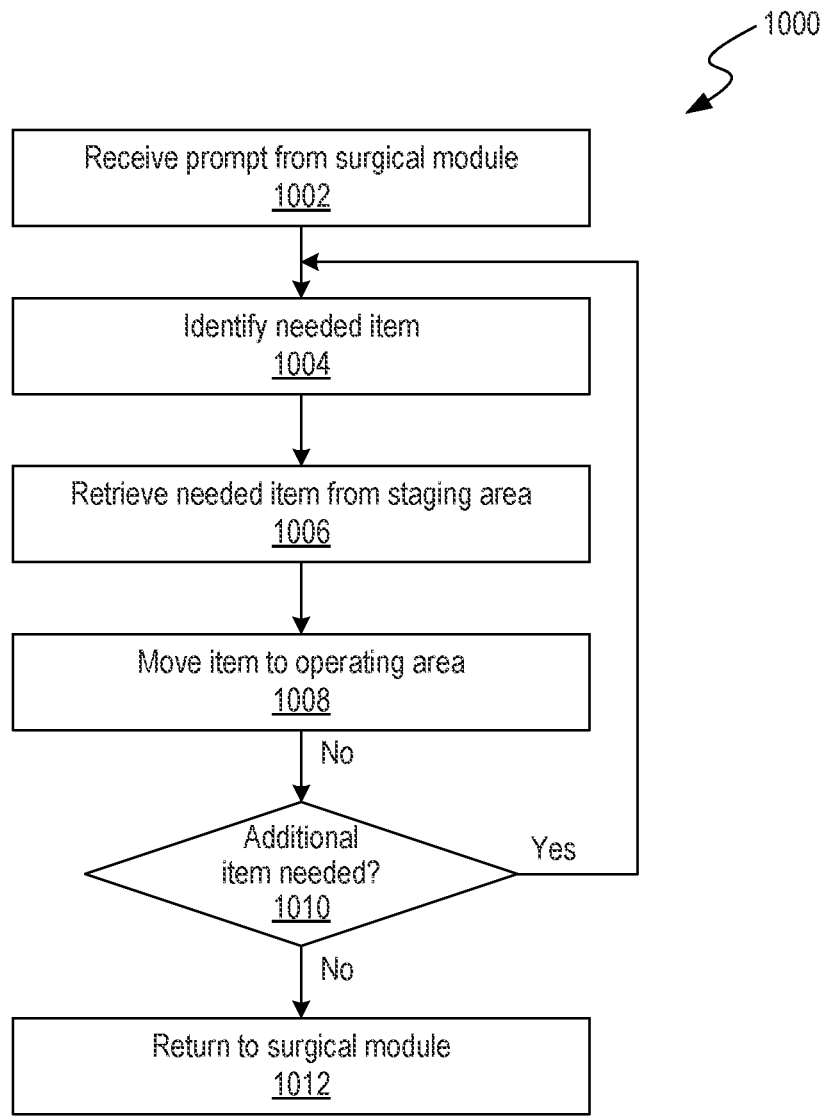
FIG. 10 is a flow diagram illustrating an example process for robotic surgical inventory management, in accordance with one or more embodiments.

FIG. 10 is a flow diagram illustrating an example process 1000 for robotic surgical inventory management, in accordance with one or more embodiments. In some embodiments, the example process 1000 is performed by the distribution module 428 illustrated and described in more detail with reference to FIG. 4. In other embodiments, the process 1000 of FIG. 10 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1002, the distribution module 428 receives a prompt from the surgical module 424. The surgical module 424 is illustrated and described in more detail with reference to FIG. 4. The prompt includes a current status of the surgical procedure and the item or items needed from the staging area 406. The staging area 406 is illustrated and described in more detail with reference to FIG. 4. In step 1004, the distribution module 128 identifies a physical position in the staging area 406 of the needed supply item. In some embodiments, an optical sensor is used with an object recognition system to identify each supply item in the staging area 406 and each supply item's position, location, or orientation. In some embodiments, the object recognition system is part of the robotic surgical system 160 illustrated and described in more detail with reference to FIG. 1. For example, a medical practitioner can identify a needed supply item using a verbal command. A scrub nurse can say "sponge" to identify the supply item needed.

In step 1006, the distribution module 428 retrieves the needed supply item from the staging area 406. A manipulator 402 can retrieve the needed supply item using a magnetic attachment, an adhesive surface, or a grasping mechanism. The manipulator 402 is illustrated and described in more detail with reference to FIG. 4. In some embodiments, the distribution module 428 delivers audible or displayed instructions to scrub nurses indicating which supply item needs to be brought to the operating area 408. In some embodiments, the robotic nurse network 414 sends a message to a manipulator 402a to move a supply from the staging area 406 to a position in the operating area 408. For example, in step 1008, the distribution module 428 moves the retrieved supply item to the appropriate position in the operating area 408 and maneuvers the supply item to the appropriate orientation to allow the supply item to be received by a medical practitioner or by the robotic surgical system 160. The robotic surgical system 160 is illustrated and described in more detail with reference to FIG. 1.

In step 1010, the distribution module 428 determines whether an additional supply item is needed in the operating area 408. If another supply item is needed, the distribution module 428 returns to step 1004. If no additional supply item is needed, the distribution module 428 returns control, at step 1012, to the surgical module 124.

Figure 11:
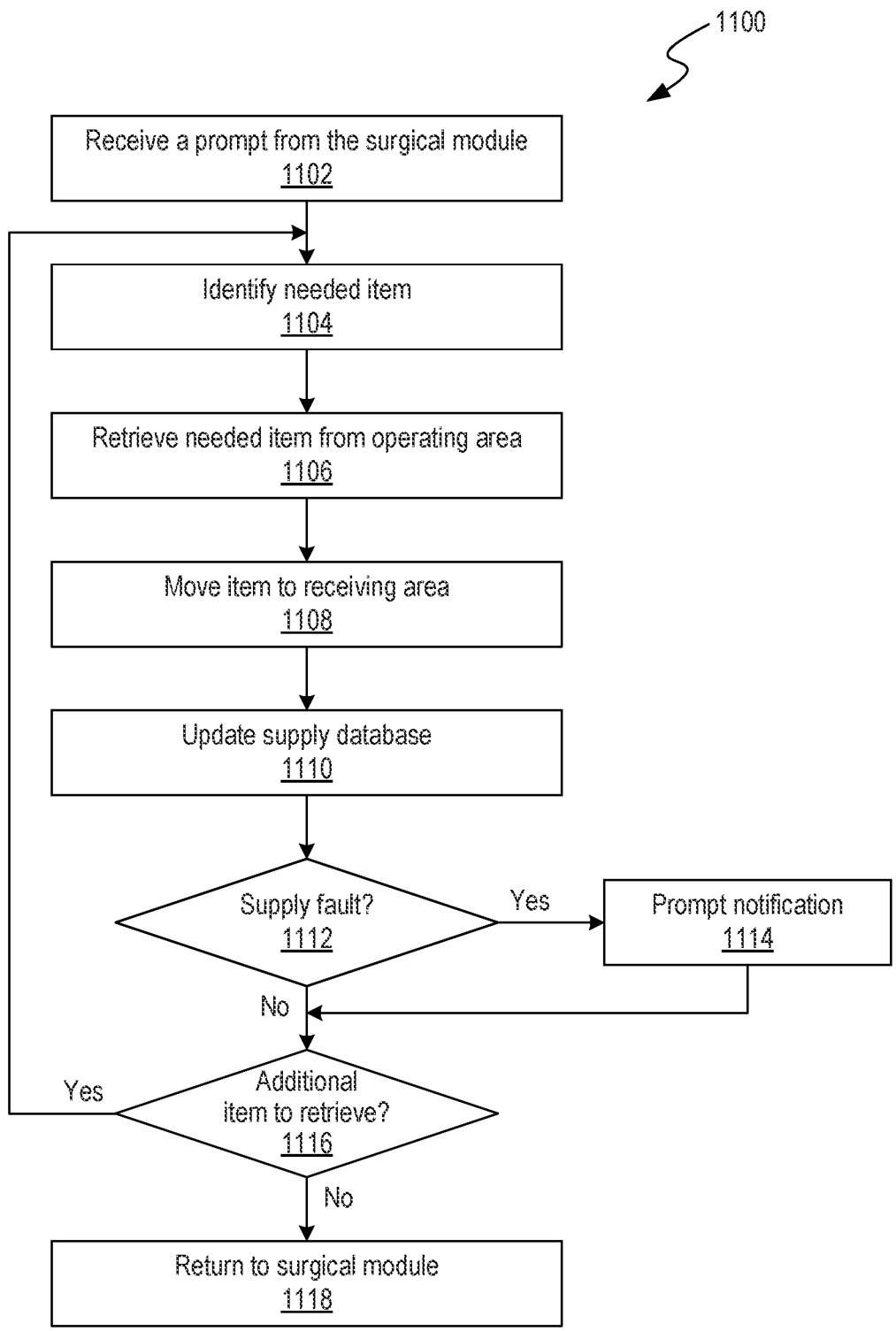
FIG. 11 is a flow diagram illustrating an example process for robotic surgical inventory management, in accordance with one or more embodiments.

FIG. 11 is a flow diagram illustrating an example process for robotic surgical inventory management, in accordance with one or more embodiments. In some embodiments, the example process 1100 is performed by the collection module 430 illustrated and described in more detail with reference to FIG. 4. In other embodiments, the process 1100 of FIG. 11 is performed by a computer system, e.g., the example computer system 300 illustrated and described in more detail with reference to FIG. 3. Particular entities, for example, the console 108 or the robotic surgical system 160 perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 1102, the collection module 430 receives a prompt from the surgical module 424. The surgical module 424 is illustrated and described in more detail with reference to FIG. 4. The prompt includes a present status of the surgical procedure and the item or items that need to be removed from the operating area 408. The operating area 408 is illustrated and described in more detail with reference to FIG. 4.

In step 1104, the collection module 430 identifies a physical position in the operating area 408 of the supply item that needs to be removed. In some embodiments, an optical sensor is used with an object recognition system to identify each supply item in the operating area 408 and each supply item's position, location, or orientation. In some embodiments, the object recognition system is part of the robotic surgical system 160 illustrated and described in more detail with reference to FIG. 1. For example, a doctor removing a sponge from a wound site can indicate that a manipulator 402 should remove that sponge from the operating area 408. The manipulator 402 is illustrated and described in more detail with reference to FIG. 4.

In some embodiments, an optical recognition system retrieves image data from one or more cameras capable of observing the doctor removing a supplied object, such as, for example, a sponge, from the surgical site. The cameras are illustrated and described in more detail with reference to FIG. 1. In some embodiments, the optical recognition system is part of the robotic surgical system 160 illustrated and described in more detail with reference to FIG. 1. The optical recognition system can then create an indicator to indicate that a manipulator 402 should remove the supplied object from the operating area 408 and/or a surgeon's hand. In other embodiments, the surgeon uses a specific gesture or other visual method to indicate to the optical recognition system that a supplied object should be removed from the operating area 408. In other embodiments, a practitioner identifies the supply item that needs to be removed using a verbal command. For example, a doctor can say "remove," which prompts a manipulator 402 to remove the supply item in the doctor's hand.

In step 1106, the collection module 430 retrieves a supply item that needs to be removed from the operating area 408. In some embodiments, a manipulator 402 retrieves the supply item using a magnetic attachment, adhesive surface, or grasping mechanism. In some embodiments, the collection module 130 sends an audible or displayed instruction to the robotic surgical system 160 or to scrub nurses indicating which supply item needs to be brought to the collection area 408. In step 1108, the retrieved supply item is moved to an appropriate position in the collection area 410. The collection area 410 is illustrated and described in more detail with reference to FIG. 4. The supply item is maneuvered to the appropriate orientation to allow the supply item counted by either a sensor 412, a medical practitioner, or a scrub nurse. The sensors 412 are illustrated and described in more detail with reference to FIG. 4.

In step 1110, with each supply item moved to the collection area 410, the collection module 430 updates the supply item's status in the supply database 416. The supply database 416 is illustrated and described in more detail with reference to FIG. 4. Step 1110 functions as a supply audit. In some embodiments, each item in the receiving area 410 is verified by more than one sensor or a combination of at least one sensor and at least one practitioner. The embodiments therefore automate the supply count. Counting each item on its way into and out of the operating area 408 by at least two sensors avoids inadvertent retention of supply items in a patient.

In some embodiments, the robotic nurse network 414 determines a supply fault based on a mismatch between a first number of supplies in a supply tray 404 and a second number of supplies in the staging area 406, the operating area 408, and the receiving area 410. The robotic nurse network 414 generates a notification based on the supply fault. For example, in step 1112, the collection module 430 determines whether there is a supply fault. A supply fault refers to a discrepancy between the number of supply items in a supply tray 404 and the total of the supply items recorded as available in the staging area 406, the operating area 408, and the receiving area 410 in the supply database 416. For example, there may be 10 sponges in a given supply tray 404a. According to the sensors 412, there are 9 sponges available: 3 in the staging area 406, 3 in the operating area 408, and 3 in the receiving area 410. The total (9) sponges accounted for in the supply database 416 does not match the quantity (10) sponges in the generic supply tray ID #123 assigned to patient Jane Doe's right knee replacement. This determined discrepancy in the count can indicate that a sponge has been inadvertently retained in the patient or that the sterile field was compromised. A supply fault can also be identified when the position of a supply item does not match the expected position of that supply item, given the surgical procedure's context. For example, there should be 5 sponges in the receiving area 410 at a given step in patient Jane Doe's right knee replacement, but only 4 can currently be determined by the sensors 412.

In step 1114, if a supply fault was detected at step 1112, the collection module 430 prompts a notification. The notification can be an audible message, an alarm, a text message, haptic feedback, or other types of prompts to the robotic surgical system 160 or a practitioner that the supply count has a discrepancy that indicates an error or problem. If there is no supply fault, the collection module 430 determines, at step 1116, whether an additional supply item needs to be removed from the operating area 408. If another supply item needs to be removed, the collection module 430 returns to step 1104. In step 1118, if no additional supply item needs to be removed from the operating area 408, the collection module 430 returns control to the surgical module 424.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

We claim:

1. A method comprising:
    identifying, by a supply monitoring surgical robot via end-effector supply imagers, a supply tray for a surgical procedure from a supply database, the identifying based on the surgical procedure and patient data retrieved from an electronic health records database;
    controlling, by the supply monitoring surgical robot a first manipulator to move a supply from the supply tray to a staging area, the supply for performing a step of a plurality of steps of the surgical procedure;
    detecting, via a first sensor integrated into the first manipulator, that the supply is needed at a present time for the step, wherein detecting the supply is needed is based on one or more real-time patient measurements, collected by one or more vital monitoring sensors, reaching a threshold;
    in response to detecting the supply is needed, identifying, via a second sensor integrated into a second manipulator, a position where the supply is needed in an operating area proximate to the staging area, wherein the supply monitoring surgical robot is configured to use the first and/or second sensors to analyze areas of interest;
    controlling, by the supply monitoring surgical robot, the second manipulator to move the supply from the staging area to the position in the operating area;
    detecting, via a third sensor integrated into a third manipulator, that the step is complete; and
    in response to detecting the step is complete, controlling, by the supply monitoring surgical robot, the third manipulator to remove the supply from the position in the operating area.

2. The method of claim 1, further comprising:
    identifying, by the supply monitoring surgical robot, a supply fault based on a mismatch between a first number of supplies in the supply tray and a second number of supplies in the staging area, the operating area, and a receiving area; and
    displaying, by the supply monitoring surgical robot, a notification based on the supply fault.

3. The method of claim 1, wherein the first manipulator is located outside a sterile field and the second manipulator is located inside the sterile field.

4. The method of claim 1, wherein the first sensor is a microphone and the microphone detects an instruction spoken by a medical practitioner.

5. The method of claim 1, wherein the first sensor is a camera and the camera captures an image, the method further comprising performing image recognition on the image to determine that the image indicates the supply.

6. The method of claim 5, wherein the image recognition is performed using a machine learning model trained on a plurality of images to generate a determination that the image indicates the supply.

7. The method of claim 5, further comprising matching the image to the plurality of steps to predict that a next supply will be needed at a next time for a next step of the plurality of steps.

8. A system comprising:
    one or more computer processors; and
    a non-transitory computer readable storage medium storing computer instructions, which when executed by the one or more computer processors, causes the one or more computer processors to:
        identify, by a supply monitoring surgical robot via end-effector supply imagers, a supply tray for a surgical procedure from a supply database, the identifying based on the surgical procedure and patient data retrieved from an electronic health records database;

control, by the supply monitoring surgical robot a first manipulator to move a supply from the supply tray to a staging area, the supply for performing a step of a plurality of steps of the surgical procedure;

detect, via a first sensor integrated into the first manipulator, that the supply is needed at a present time for the step, wherein detecting the supply is needed is based on one or more real-time patient measurements, collected by one or more vital monitoring sensors, reaching a threshold;

in response to detecting the supply is needed, identify, via a second sensor integrated into a second manipulator, a position where the supply is needed in an operating area proximate to the staging area, wherein the supply monitoring surgical robot is configured to use the first and/or second sensors to analyze areas of interest;

control, by the supply monitoring surgical robot, the second manipulator to move the supply from the staging area to the position in the operating area;

detect, via a third sensor integrated into a third manipulator, that the step is complete; and in response to detecting the step is complete, control, by the supply monitoring surgical robot, the third manipulator to remove the supply from the position in the operating area.

9. The system of claim 8, wherein the computer instructions, which when executed by the one or more computer processors further cause the one or more computer processors to:

identify, by the supply monitoring surgical robot, a supply fault based on a mismatch between a first number of supplies in the supply tray and a second number of supplies in the staging area, the operating area, and a receiving area; and display, by the supply monitoring surgical robot, a notification based on the supply fault.

10. The system of claim 8, wherein the first manipulator is located outside a sterile field and the second manipulator is located inside the sterile field.

11. The system of claim 8, wherein the first sensor is a microphone and the microphone detects an instruction spoken by a medical practitioner.

12. The system of claim 8, wherein the first sensor is a camera and the camera captures an image, wherein the computer instructions, which when executed by the one or more computer processors further cause the one or more computer processors to perform image recognition on the image to determine that the image indicates the supply.

13. The system of claim 12, wherein the image recognition is performed using a machine learning model trained on a plurality of images to generate a determination that the image indicates the supply.

14. The system of claim 12, wherein the computer instructions, which when executed by the one or more computer processors further cause the one or more computer processors to match the image to the plurality of steps to predict that a next supply will be needed at a next time for a next step of the plurality of steps.

15. A non-transitory computer readable storage medium storing computer instructions, which when executed by one or more computer processors, causes the one or more computer processors to:

identify, by a supply monitoring surgical robot via end-effector supply imagers, a supply tray for a surgical procedure from a supply database, the identifying based on the surgical procedure and patient data retrieved from an electronic health records database;

control, by the supply monitoring surgical robot a first manipulator to move a supply from the supply tray to a staging area, the supply for performing a step of a plurality of steps of the surgical procedure;

detect, via a first sensor integrated into the first manipulator, that the supply is needed at a present time for the step, wherein detecting the supply is needed is based on one or more real-time patient measurements, collected by one or more vital monitoring sensors, reaching a threshold;

in response to detecting the supply is needed, identify, via a second sensor integrated into a second manipulator, a position where the supply is needed in an operating area proximate to the staging area, wherein the supply monitoring surgical robot is configured to move the first and/or second sensors to analyze areas of interest;

control, by the supply monitoring surgical robot, a second manipulator to move the supply from the staging area to the position in the operating area;

detect, via a third sensor integrated into a third manipulator, that the step is complete; and in response to detecting the step is complete, control, by the supply monitoring surgical robot, the third manipulator to remove the supply from the position in the operating area.

16. The non-transitory computer readable storage medium of claim 15, wherein the computer instructions, which when executed by the one or more computer processors further cause the one or more computer processors to:

identify, by the supply monitoring surgical robot, a supply fault based on a mismatch between a first number of supplies in the supply tray and a second number of supplies in the staging area, the operating area, and a receiving area; and display, by the supply monitoring surgical robot, a notification based on the supply fault.

17. The non-transitory computer readable storage medium of claim 15, wherein the first manipulator is located outside a sterile field and the second manipulator is located inside the sterile field.

18. The non-transitory computer readable storage medium of claim 15, wherein the first sensor is a microphone and the microphone detects an instruction spoken by a medical practitioner.

19. The non-transitory computer readable storage medium of claim 15, wherein the first sensor is a camera and the camera captures an image, wherein the computer instructions, which when executed by the one or more computer processors further cause the one or more computer processors to perform image recognition on the image to determine that the image indicates the supply.

20. The non-transitory computer readable storage medium of claim 19, wherein the image recognition is performed using a machine learning model trained on a plurality of images to generate a determination that the image indicates the supply.

\* \* \* \* \*